United States Patent [19]

Witzel et al.

[11] Patent Number: 5,705,699
[45] Date of Patent: Jan. 6, 1998

[54] PREPARATION OF 3-AMINOMETHYL-3,5,5-TRIMETHYLCYCLOHEXYLAMINE

[75] Inventors: Tom Witzel, Ludwigshafen; Guido Voit, Schriesheim, both of Germany

[73] Assignee: BASF Aktiengesellschaft, Ludwigshafen, Germany

[21] Appl. No.: 395,323

[22] Filed: Feb. 28, 1995

[30] Foreign Application Priority Data

Mar. 4, 1994 [DE] Germany .......................... 44 07 325.9

[51] Int. Cl.$^6$ ..................................................... C07C 209/16
[52] U.S. Cl. .......................................... 564/446; 564/448
[58] Field of Search ....................................... 564/448, 446

[56] References Cited

U.S. PATENT DOCUMENTS

| | | |
|---|---|---|
| 3,352,913 | 11/1967 | Schmitt et al. . |
| 4,248,799 | 2/1981 | Drake .......................... 564/491 |
| 4,429,157 | 1/1984 | Disteldorf et al. . |
| 5,011,968 | 4/1991 | Thunberg et al. . |
| 5,286,906 | 2/1994 | Hara et al. ..................... 564/446 |
| 5,371,292 | 12/1994 | Merger et al. ................. 564/446 |
| 5,406,000 | 4/1995 | Forquy ........................... 564/446 |
| 5,491,264 | 2/1996 | Herkes et al. ................. 558/431 |

FOREIGN PATENT DOCUMENTS

| | | |
|---|---|---|
| 2039328 | 10/1991 | Canada . |
| 2062267 | 9/1992 | Canada . |
| 2105100 | 3/1994 | Canada . |
| 0394967 | 10/1990 | European Pat. Off. . |
| 590419 | 4/1994 | European Pat. Off. . |
| 3011656 | 10/1981 | Germany . |
| 1047920 | 11/1966 | United Kingdom . |

*Primary Examiner*—Brian M. Burn
*Attorney, Agent, or Firm*—John H. Shurtleff

[57] ABSTRACT

3-Aminomethyl-3,5,5-trimethylcyclohexylamine is prepared by reacting 3-cyano-3,5,5-trimethylcyclohexanone with 3-aminomethyl-3,5,5-trimethylcyclohexylamine and subsequently or simultaneously adding ammonia under a hydrogen pressure of from 50 to 300 bar in the presence of a hydrogenation catalyst at from 20° to 150° C., by a process in which the reaction is carried out without removing the water of reaction.

7 Claims, No Drawings

PREPARATION OF 3-AMINOMETHYL-3,5,5-TRIMETHYLCYCLOHEXYLAMINE

The present invention relates to a process for the preparation of 3-aminomethyl-3,5,5-trimethylcyclohexylamine (isophoronediamine, IPDA) by reacting 3-cyano-3,5,5-trimethylcyclohexanone (isophoronenitrile, IPN) with isophoronediamine and subsequently or simultaneously adding ammonia under a hydrogen pressure of from 50 to 300 bar in the presence of a hydrogenation catalyst without removing the water of reaction.

The preparation of 3-aminomethyl-3,5,5-trimethylcyclohexylamine by reductive amination of 3-cyano-3,5,5-trimethylcyclohexanone (obtainable from hydrogen cyanide and isophorone, for example according to DE-A-12 40 854, U.S. Pat. No. 5,011,968) is generally known. In particular, 3-aminomethyl-3,5,5-trimethylcyclohexanol (amino alcohol, IPAA), 1,3,3-trimethyl-6-azabicyclo[3.2.1]octane (bicyclic compound), 3-cyano-3,5,5-trimethylcyclohexylamine (aminonitrile, IPNA) and the cleavage products 3,5,5-trimethylcyclohexanol and 3,5,5-trimethylcyclohexylamine, formed by elimination of hydrocyanic acid, are mentioned as byproducts.

In DE-A-12 29 078, yields of up to 81.4% are stated for the use of from 10 to 30 mol of ammonia per mol of 3-cyano-3,5,5-trimethylcyclohexanone over a cobalt catalyst (33% on Kieselguhr) in the batchwise procedure in a stirred autoclave at 150 bar and 120° C. The reaction is carried out in an organic solvent, for example in 1 kg of methanol per kg of 3-cyano-3,5,5-trimethylcyclohexanone. According to DE-A-41 06 882, the yields proved to be nonreproduceable.

In an attempt to increase the yield, in DE-A-30 21 955 the reaction is carried out in two stages at from 250 to 300 bar and with an excess of ammonia of from 10 to 30 mol/mol (up to 95% yield). Here, organic or inorganic ion exchangers in the ammonium form are used in the first stage in order to achieve imination of the ketofunction. The imine formed from ammonia and 3-cyano-3,5,5-trimethylcyclohexanone is then converted into 3-aminomethyl-3,5,5-trimethylcyclohexylamine in a second stage by hydrogenation over conventional cobalt catalysts.

If, as described in DE-A-30 11 656, the imination is carried out without a catalyst, ie. purely thermally, both the selectivity and the space-time yield are substantially poorer. DE-A-40 10 227 describes the preparation of 3-aminomethyl-3,5,5-trimethylcyclohexylamine likewise by a two-stage process, the imination being carried out over acidic metal oxides and the hydrogenation preferably over base-doped hydrogenation catalysts. Yields of from 95 to 98% are obtained.

According to DE-A-41 06 882, an additional cocatalyst in the form of a salt (for example 50 g of cobalt chloride hexahydrate on 100 g of Raney cobalt and 400 g of 3-cyano-3,5,5-trimethylcyclohexanone) is required in the preparation of 3-aminomethyl-3,5,5-trimethylcyclohexylamine from 3-cyano-3,5,5-trimethylcyclohexanone under aminating and hydrogenating conditions over Raney cobalt or Raney nickel in order to achieve high selectivities, the yield being 85%. Other disadvantages of this process are the use of an organic solvent (for example 2 kg/kg of 3-cyano-3,5,5-trimethylcyclohexanone) and the difficult recovery of the corrosive catalyst/cocatalyst system.

EP-A-394 967 discloses a process for the preparation of 3-aminomethyl-3,5,5-trimethylcyclohexylamine, in which a number of measures must be complied with to suppress the direct hydrogenation of the carbonyl function to the alcohol with formation of 3-aminomethyl-3,5,5-trimethylcyclohexanol and the elimination of hydrocyanic acid with formation of 3,5,5-trimethylcyclohexanol and 3,5,5-trimethylcyclohexylamine:

two-stage and multistage procedure with stepwise change in pressure and temperature
  addition of alcohols as amination promoters
  shifting of the imination equilibrium by separating off the water of reaction In the imination with ammonia, the last measure is not possible owing to the boiling points. It is therefore proposed to adopt a route in which IPN is first iminated with a high-boiling amine, for example IPDA and then, after removal of the water of reaction, transimination is first effected with ammonia and hydrogenation is then carried out with a stepwise temperature change in a multistage procedure.

The combination of all measures proposed in EP-A-394 967 leads to a maximum yield of 90% in conjunction with a low space-time yield.

It is an object of the present invention to remedy the above-mentioned disadvantages.

We have found that this object is achieved by a novel and improved process for the preparation of 3-aminomethyl-3,5,5-trimethylcyclohexylamine by reacting 3-cyano-3,5,5-trimethylcyclohexanone with 3-aminomethyl-3,5,5-trimethylcyclohexylamine and subsequently or simultaneously adding ammonia under a hydrogen pressure of from 50 to 300 bar in the presence of a hydrogenation catalyst at from 20° to 150° C., which comprises carrying out the reaction without removing the water of reaction.

The novel process is noteworthy in that, in view of EP-A-394 967, it was not to be expected that selectivities of up to 94% are achievable without removing the water of reaction or other factors having a positive effect on the imination equilibrium and essentially without adding a solvent. Also noteworthy is the minimum amount of high-boiling components, although a process stage involving the transimination with ammonia, as stated in EP-A-394 967, was dispensed with.

The process can be carried out in one or two stages [1st stage condensation of 3-cyano-3,5,5-trimethylcyclohexanone with 3-aminomethyl-3,5,5-trimethylcyclohexylamine (imination), 2nd stage hydrogenation with transimination] over a commercial hydrogenation catalyst without removing the water of reaction and preferably essentially in the absence of an additional solvent. A one-stage procedure is preferred.

In the one-stage procedure, 3-cyano-3,5,5-trimethylcyclohexanone and 3-aminomethyl-3,5,5-trimethylcyclohexylamine in a molar ratio of from 0.5:1 to 5:1, preferably from 0.8:1 to 2:1, particularly preferably from 1:1, can be reacted at from 50° to 150° C., preferably from 80° to 130° C., with the addition of ammonia to the 3-cyano-3,5,5-trimethylcyclohexanone in a weight ratio of from 0.1:1 to 10:1, preferably from 0.2:1 to 2:1, at a hydrogen pressure of from 50 to 300, preferably from 100 to 250, bar, either batchwise in an autoclave or loop reactor over a suspended catalyst (from 10 to 50, preferably from 20 to 40, particularly preferably from 25 to 35, % by weight) or continuously in a tube reactor over a fixed-bed catalyst (at space velocities of from 0.05 to 0.5, preferably from 0.1 to 0.2, kg per 1 per h), preferably batchwise in an autoclave.

The two-stage procedure can be carried out either at different times in an autoclave or loop reactor or at different points in space, the condensation being carried out in the presence or absence of a catalyst, preferably in the absence of a catalyst, either continuously in a stirred cascade or in a tube reactor or batchwise in a stirred kettle, and the subsequent hydrogenation being carried out continuously in a stirred kettle cascade (using a suspended catalyst) or in a tube reactor (using a heterogeneous catalyst) or batchwise in a stirred kettle (using a suspended catalyst). The time-based two-stage procedure in an autoclave or loop reactor is preferred. Here, 3-cyano-3,5,5-trimethylcyclohexanone and 3-aminomethyl-3,5,5-trimethylcyclohexylamine in a molar ratio from 0.5:1 to 5:1, preferably from 0.8:1 to 2:1, particularly preferably 1:1, are stirred at from 20° to 100° C., preferably from 40° to 60° C., for from 0.5 to 3, preferably from 1 to 2, hours and, after the addition of the suspension catalyst (from 10 to 50, preferably 30, % by weight) and of from 0.1 to 10, preferably from 0.2 to 2, kg of ammonia per kg of 3-cyano-3,5,5-trimethylcyclohexanone, are reacted at a hydrogen pressure of from 50 to 300, preferably from 100 to 250, bar and a hydrogenation temperature of from 50° to 150° C., preferably from 80° to 130° C.

The hydrogenation catalysts used may be, as a rule, all commercial hydrogenation catalysts which contain one or more of the elements from the group consisting of copper or elements of subgroup VIII of the Periodic Table of Elements, preferably nickel, cobalt, iron, copper and/or ruthenium. Depending on the application, the catalysts are used as suspension or fixed-bed catalysts (unsupported catalysts or supported catalysts). Raney nickel or Raney cobalt is preferably used in the form of a suspension catalyst, and unsupported or supported cobalt Catalysts are preferably used as fixed-bed catalysts. Suitable carriers are silica, alumina, titanium dioxide, active carbon and zeolites.

The novel process is carried out essentially in the absence of an (additional) solvent, for example of an alcohol and/or of a hydrocarbon. As a rule, the amount of the additional solvent is from 0 to 10, preferably from 0 to 5, % by weight, and particularly preferably no additional solvent (0% by weight) is used.

3-Aminomethyl-3,5,5-trimethylcyclohexylamine is used as a starting material for the preparation of isophorone diisocyanates, as an amine component for polyamides and as a curing agent for epoxy resins.

EXAMPLES

Example 1

In a stirred flask, 165 g (1 mol) of 3-cyano-3,5,5-trimethylcyclohexanone were stirred together with 170 g (1 mol) of 3-aminomethyl-3,5,5-trimethylcyclohexylamine for 2 hours at 50° C. The melt-like discharged mixture was then transferred to a stirred autoclave having a gassing stirrer and, after the addition of 100 g of Raney cobalt and 560 ml (20 mol) of liquid ammonia, was reacted for 10 hours at 100° C. and a hydrogen pressure of 250 bar.

The discharged hydrogenation mixture contained:

| | |
|---|---|
| 3-aminomethyl-3,5,5-triethylcyclohexylamine | 97.0% by weight |
| 1,3,3-trimethyl-6-azabicyclo[3.2.1]octane | 1.9% by weight |
| 3-aminomethyl-3,5,5-trimethylcyclohexanol | 0.2% by weight |
| Cleavage products | 0.3% by weight |

The yield based on 3-cyano-3,5,5-trimethylcyclohexanone was 94.1%.

Example 2

In a stirred flask, 165 g (1 mol) of 3-cyano-3,5,5-trimethylcyclohexanone were stirred together with 170 g (1 mol) of 3-aminomethyl-3,5,5-trimethylcyclohexylamine for 2 hours at 50° C. The melt-like discharged mixture was then transferred to a stirred autoclave having a gassing stirrer and, after the addition of 100 g of Raney cobalt and 560 ml (20 mol) of liquid ammonia, was reacted for 10 hours at 130° C. and a hydrogen pressure of 115 bar.

The discharged hydrogenation mixture contained:

| | |
|---|---|
| 3-aminomethyl-3,5,5-trimethylcyclohexylamine | 95.6% by weight |
| 1,3,3-trimethyl-6-azabicyclo[3.2.1]octane | 2.5% by weight |
| 3-cyano-3,5,5-trimethylcyclohexylamine | 2.0% by weight |
| Cleavage products | 0.4% by weight |

The yield based on 3-cyano-3,5,5-trimethylcyclohexanone was 91.2%.

Example 3

In a stirred flask, 165 g (1 mol) of 3-cyano-3,5,5-trimethylcyclohexanone were stirred together with 170 g (1 mol) of 3-aminomethyl-3,5,5-trimethylcyclohexylamine for 2 hours at 50° C. The melt-like discharged mixture was then transferred to a stirred autoclave having a gassing stirrer and, after the addition of 100 g of Raney cobalt and 210 ml (7.4 mol) of liquid ammonia, was reacted for 10 hours at 130° C. and a hydrogen pressure of 150 bar.

The discharged hydrogenation mixture contained:

| | |
|---|---|
| 3-aminomethyl-3,5,5-trimethylcyclohexylamine | 95.8% by weight |
| 1,3,3-trimethyl-6-azabicyclo[3.2.1]octane | 3.5% by weight |
| 3-aminomethyl-3,5,5-trimethylcyclohexanol | 0.3% by weight |
| Cleavage products | 0.5% by weight |

The yield based on 3-cyano-3,5,5-trimethylcyclohexanone was 91.6%.

Example 4

In a stirred autoclave having a gassing stirrer, 165 g (1 mol) of 3-cyano-3,5,5-trimethylcyclohexanone were reacted with 170 g (1 mol) of 3-aminomethyl-3,5,5-trimethylcyclohexylamine for 10 hours at 100° C. and a hydrogen pressure of 250 bar after the addition of 100 g of Raney cobalt and 560 ml (20 mol) of liquid ammonia.

The discharged hydrogenation mixture contained:

| | |
|---|---|
| 3-aminomethyl-3,5,5-trimethylcyclohexylamine | 96.6% by weight |
| 1,3,3-trimethyl-6-azabicyclo[3.2.1]octane | 2.9% by weight |
| 3-cyano-3,5,5-trimethylcyclohexylamine | 0.05% by weight |
| 3-aminomethyl-3,5,5-trimethylcyclohexanol | 0.05% by weight |
| Cleavage products | 0.3% by weight |

The yield based on 3-cyano-3,5,5-trimethylcyclohexanone was 93.1%.

The analysis (% by weight) of the discharged hydrogenation mixtures was carried out in a capillary column (25 m OV1, 80-15-280).

We claim:

1. A process for the preparation of 3-aminomethyl-3,5,5-trimethylcyclohexylamine which comprises reacting 3-cyano-3,5,5-trimethyl-cyclohexanone (IPN) with 3-aminomethyl-3,5,5-trimethylcyclohexylamine (IPDA) in two sequential steps:

first, in a molar ratio of IPDA:IPN of at least 0.5:1 at an elevated temperature without removing the water of reaction; and second, adding ammonia and maintaining a hydrogen pressure of from 50 to 300 bar in the presence of a hydrogenation catalyst and at a temperature of from 20° to 150° C.

2. A process as claimed in claim 1, wherein the molar ratio of IPDA:IPN is from 0.5:1 to 5:1.

3. A process as claimed in claim 1, wherein ammonia and IPN are reacted in a weight ratio of from 0.1:1 to 10:1.

4. A process as claimed in claim 1, wherein the hydrogenation catalyst contains at least one element selected from the group consisting of copper and the elements of Group VIII of the Periodic Table of Elements.

5. A process as claimed in claim 4, wherein said hydrogenation catalyst is selected from the group consisting of Raney cobalt and Raney nickel.

6. A process as claimed in claim 4, wherein said hydrogenation catalyst consists essentially of a supported or unsupported cobalt catalyst.

7. A process as claimed in claim 1, wherein the entire reaction is carried out essentially in the absence of any organic solvent.

* * * * *